United States Patent
Sadeghi

(10) Patent No.: US 10,849,782 B1
(45) Date of Patent: Dec. 1, 2020

(54) ANTI-SNORING TRAMPOLINE PILLOW

(71) Applicant: Mohsen Esmail Sadeghi, Richardson, TX (US)

(72) Inventor: Mohsen Esmail Sadeghi, Richardson, TX (US)

(73) Assignee: Mohsen E. Sadeghi, Plano, TX (US)

( * ) Notice: Subject to any disclaimer, the term of this patent is extended or adjusted under 35 U.S.C. 154(b) by 222 days.

(21) Appl. No.: 15/972,313

(22) Filed: May 7, 2018

(51) Int. Cl.
*A61F 5/56* (2006.01)
*A47G 9/10* (2006.01)

(52) U.S. Cl.
CPC .............. *A61F 5/56* (2013.01); *A47G 9/1009* (2013.01); *A47G 9/109* (2013.01)

(58) Field of Classification Search
CPC ...... A47G 9/1009; A47C 31/023; A47C 16/00
USPC ....................................... 297/452.13, 452.56
See application file for complete search history.

(56) References Cited

U.S. PATENT DOCUMENTS

| | | | | |
|---|---|---|---|---|
| 2,551,727 A * | 5/1951 | Costello | ............... | A47C 20/026 5/638 |
| D318,735 S * | 7/1991 | Draxler | ............................ | 5/636 |
| 5,608,935 A * | 3/1997 | Warfield | ............. | A47G 9/1009 5/639 |
| 6,581,226 B1 * | 6/2003 | Brustein | ............. | A47G 9/1009 5/636 |
| 2013/0062924 A1 * | 3/2013 | Caldwell | ............. | A47C 31/023 297/452.63 |

* cited by examiner

Primary Examiner — Sarah B McPartlin

(57) ABSTRACT

An anti-snoring trampoline pillow is a highbred apparatus constructed in a substantially rectangular configuration that is a head supporting device and pillow which enables a person to rest or sleep on. The device provides improvement in two important key areas to deliver its superior advantages. On the one hand, the pillow provides an elastically aided rebounding headrest surface area to prevent the said pillow from going flat, causing adverse and improper head/neck posture while on the other hand, and the person's head position may be guided in variety of supported posture to reduce snoring by utilizing customized attachable headrest cushion modules to the rebounding headrest surface platform. It is crucial to keep our mind and body healthy by maintaining high levels of quality sleep during our rest time.

8 Claims, 4 Drawing Sheets

ANTI-SNORING TRAMPOLINE PILLOW

BACKGROUND OF THE INVENTION

Field of the Invention

The current invention relates to an apparatus that is a head supporting device and pillow which enables a person to rest or sleep on with customize attachable components to support head and neck position aiming to reduce posture related snoring issues.

Background Art

Snoring happens when you can't move air freely through your nose and throat during sleep. This makes the surrounding tissues vibrate, which produces the familiar snoring sound. People who snore often have too much throat and nasal tissue or floppy tissue that is more prone to vibrate. Although snoring could be the results of many factors, some of the most common causes of snoring can be listed as: Age, Being overweight or out of shape, The way our body is built, Nasal and sinus problems, The use of alcohol, some medications, smoking and finally sleep posture.

There are many prior arts that are designed to solve this common posture related snoring problem.

There are known anti-snoring pillows and devices such that (Anti-snoring pillow KR101333221B1, "The present invention relates to an anti-snoring pillow which comprises: a belt-shaped head support part which supports the head of a human body during a sleep; a pair of rollers which are installed inside the head support part and allow the head support part to move on rails; a support part which rotationally supports the rollers; and a control part which is installed on one side of the support part and controls the rollers. The pillow prevents snoring and induces a sound sleep.")

There are known Orthopedic pillow aiming to reduce snoring; (Orthopedic pillow which minimizes snoring U.S. Pat. No. 4,850,067A, "An orthopedic pillow which enhances muscular relaxation during sleep and which minimizes snoring is constituted by a soft compressible material which underlies the head, nape of the neck and shoulders of a sleeper lying on his back. This pillow is generally rectangular in plan view and has its upper surface contoured to provide laterally spaced upstanding side margins at each side of a body-supporting central region. The central region has a centrally positioned nape-supporting portion of greatest elevation convexly curved from top to bottom and concavely curved from side to side to support the nape of the neck. The nape-supporting portion separates: (1) a side to side concave portion at the upper end of said pillow which is inclined downwardly from its highest point at said nape-supporting portion to a low point at the occipital portion of the head for supporting the back of the head; from (2) a second portion at the lower end of said pillow for supporting the upper portion of the back which is inclined downwardly from its highest point at said nape-supporting portion to a lower end of minimum elevation. The back-supporting inclined portion is bordered at both sides thereof by shoulder-receiving depressions where the pillow is of minimum thickness.")

There are known anti-snoring pillow such that; (Anti-snoring pillow U.S. Pat. No. 7,100,227B2, "An anti-snoring pillow having a top pillow, a bottom pillow, and a covering is provided. The bottom pillow has a top surface angled with respect to a bottom surface. The top surface of the bottom pillow has a head-receiving cavity defined therein. The covering has a top section, a middle section, and a bottom section. The top pillow is in the top section and the bottom pillow is in the bottom section. The middle section maintains the top pillow centered over the head-receiving cavity during use.")

One of the most obvious problems these prior arts have in common is the concept of "one size fits all", while it is obvious human's body greatly differs in size and shape from one to the other, therefore the unique solution provided by prior arts clearly demonstrate the inability to accommodate scenarios beyond their original design.

Therefore there is a need for an anti-snoring trampoline pillow apparatus that on one part having means of being flexible, tension adjustable to accommodate different body size and head weight, and on the other part having means of attachable customized in shape and texture headrest cushion components to safeguard the neck and head position to reduce snoring caused by body posture during sleep time.

SUMMARY OF THE INVENTION

In view of the foregoing disadvantages inherent in the known types of anti-snoring pillows mainly limited to provide a "one solution fits all" concept, the present invention provides a new approach and methods to deliver a multi-functional apparatus to address every unique scenario that relates to body and head posture related causes of snoring.

The general purpose of the present invention, which will be described subsequently in greater detail, is to provide a new solution and avoid the limitations set forth by previous arts. The apparatus and method which has many of the advantages of anti-snoring pillows of prior arts mentioned heretofore and many novel features that result in a new anti-snoring trampoline pillow with attachable customized headrest cushions which is not anticipated, rendered obvious, suggested, or even implied by any of the prior art anti-snoring pillows, either alone or in any combination thereof.

One novel aspect of the preferred embodiment is the use of a controllable elastic band and its plurality of tension members that are horizontally extended-out. This approach will prevent the anti-snoring trampoline pillow from going flat and loose its head and neck support the way most conventional pillows do. This arrangement is simple and inexpensive to implement, while significantly enhancing the flexible support response that is provided by its rebounding base headrest surface.

The said controllable surface rebounding feature of the base headrest can be achieved through utilization of variant combination of the elastic band thickness, the band elasticity strength characterization and the number of its said tension members. In a preferred embodiment, the combination of referenced features as discussed above could provide the users with a choice to select a comfort performance level described herein as soft, medium or firm to best match the desired head and neck support in order to minimize the body posture related snoring issues.

Another novel aspect of the preferred embodiment of the current invention is the customized detachable headrest cushions fastened to the base headrest rebounding surface. This approach will give the user the ability to select a customized cushion best suited for their snoring condition by selecting an appropriate shape, height, firmness or orientation of the said headrest cushions.

To attain this, the present invention generally comprises of a rigid shaped frame preferably in a substantially rectangular configuration, elastic bands, connector zipper, perforated base headrest and attachable customized headrest cushions.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Such variation in design could include an embodiment where there are no elastic bands and expansion type spring is utilized to provide the same functionality and concept.

Furthermore the embodiments are not limited to one particular industry or group of people; they could be easily applied to other industries such as furniture, Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new anti-snoring trampoline pillow apparatus and method which has many of the advantages of the prior anti-snoring pillows which may improve snoring heretofore and many novel features that result in a multi-functional anti-snoring trampoline pillow which is not anticipated, rendered obvious, suggested, or even implied by any of the prior art anti-snore pillow system which offers anti-snoring solution, either alone or in any combination thereof.

One or more embodiments of the present invention provide an anti-snoring trampoline pillow that is modular allowing any and all of its major components to be interchangeable. The major components can be referenced as; frame, elastic bands, inner connecting zipper, flat perforated center base and the attachable customized headrest cushion components.

According to one or more embodiments of the present invention, an anti-snoring trampoline pillow comprises of a rigid shaped frame that would surround the person's head covering the right side, left side and top side with respect to the position of the person's head and an opening at the bottom where the person's neck comes in contact with center base. This type of frame is commonly referenced as "C" shape frame. The frame further comprises of channels embedded, extruded on its interior wall side positioned in variance of 1-10 inches above the base of the frame. Furthermore, the said extruded channel preferably 4 inches above the base of the frame would allow the elastic band's tension members to be slide in/out at ease for installation or replacement purposes.

According to the above embodiments of the present invention, an anti-snoring trampoline pillow comprises of elastic bands component able to resume its normal shape spontaneously after contraction, dilatation, or distortion due to forces exerted by the weight of person's head and neck. The said elastic bands can demonstrate variety of pulling strength based on characteristics of its thickness, number of bands and its material make-up composition.

According to one or more embodiments of the present invention, the anti-snoring trampoline pillow comprises the means of a center base component. The said center base generally provides the main headrest area that is said to be perforated to allow air circulation through and maximize the comfort sensation. The said center base module would also accommodate the means of attachment mechanism for the headrest cushion modules to be added or remove. The said center base would have the means of varying in material composition, size, shape, color, strength and performance capabilities.

According to one or more embodiments of the present invention, the anti-snoring trampoline pillow comprises the means of fastening mechanism to join the elastic band modules and the center base modules. Said fasten mechanism could utilize; zippers, hooks, loops, clips, hinges, magnets or any other types and combinations of fasten that are commercially available. A preferred said fasten mechanism could be of a zipper type that allows the zipper tape from one side having the means of being attached, to the elastic band modules and from the other side of zipper tape attached to the center based. The said fasten mechanism will allow the jointed components to be able to disengage from one another in any event that requires such an action.

DESCRIPTION OF THE PREFERRED EMBODIMENTS

Hereafter, an embodiment of the invention will be described. In embodiment of the invention, numerous specific details are set forth in order to provide a more thorough understanding of the invention. However, it will be apparent to one of ordinary skill in the art that the invention may be practiced without these specific details. In other instances, well-known features have not been described in detail to avoid obscuring the invention.

Figure 1:
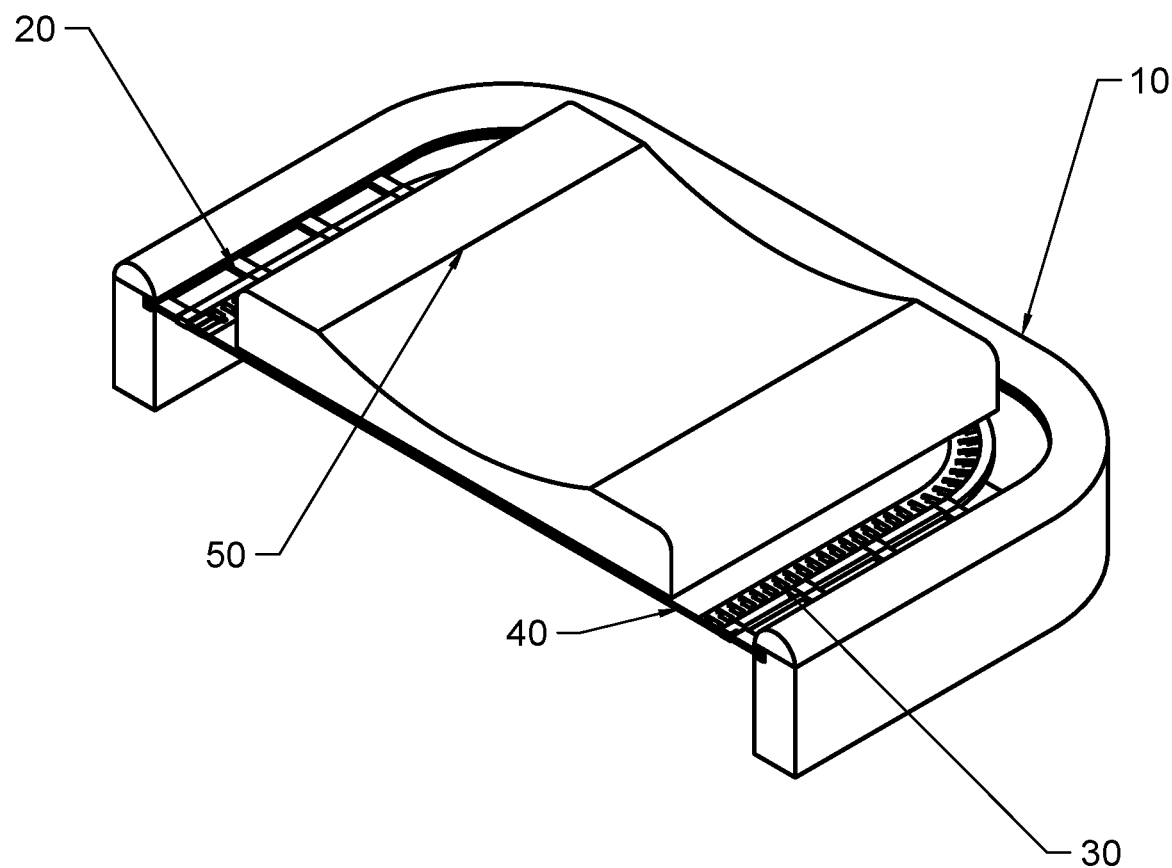
FIG. 1 illustrates a front south-west view of the anti-snoring trampoline pillow of the present invention.

Referring now to the drawings, in FIG. 1, the apparatus of the invention comprises a shaped rigid frame, denoted generally by reference numeral 10. In the preferred embodiment, at least the top of frame 10 is covered with a resilient foam material to help cushion any impact against the frame. A detachable, replaceable elastic band denoted generally by reference numeral 20, a zipper denoted generally by reference numeral 30, a base headrest denoted generally by reference numeral 40 a customized shaped headrest cushion component with means and ability to be attached or removed from the base headrest denoted generally by reference numeral 50.

Figure 2:
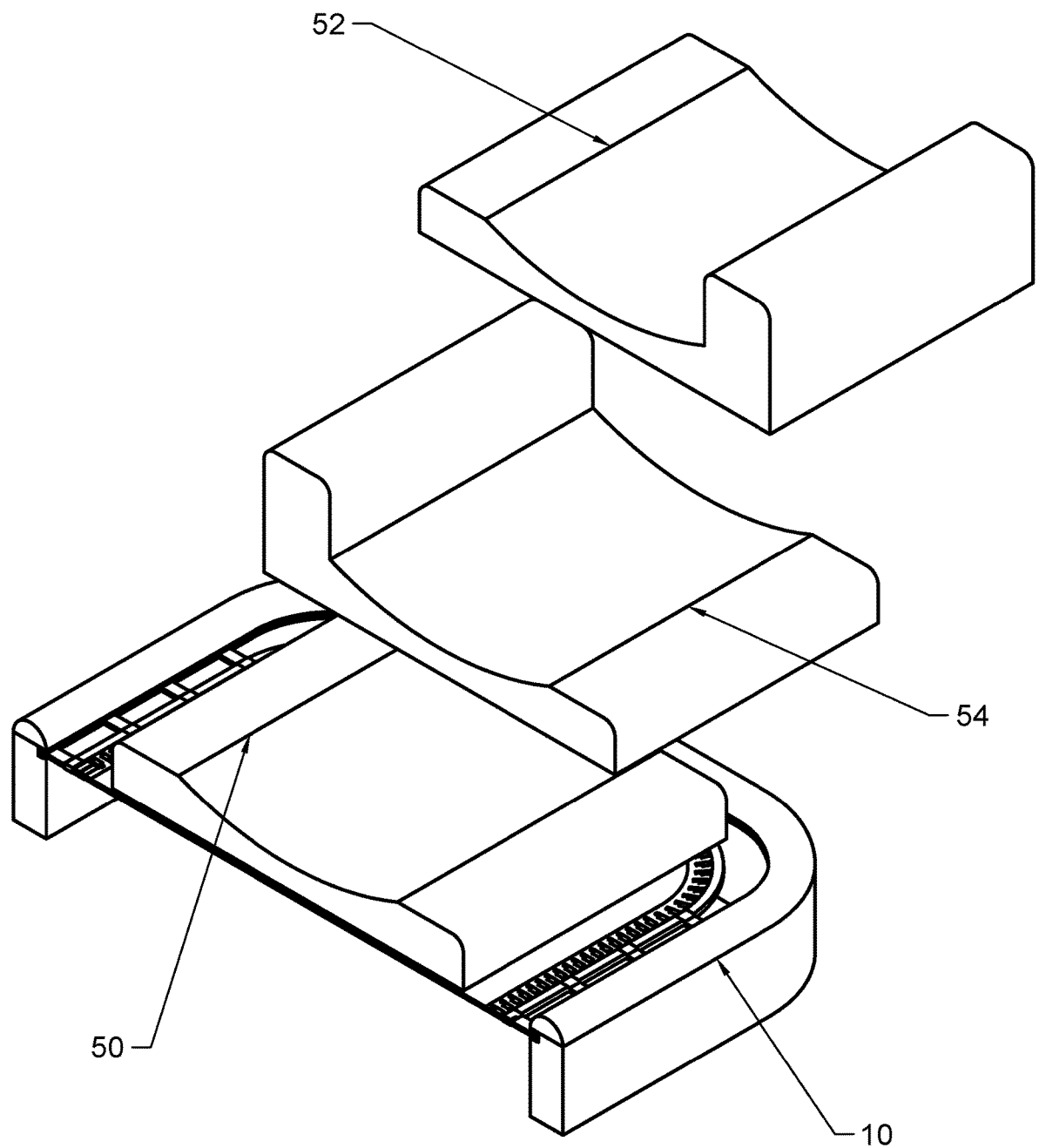
FIG. 2 illustrates an exploded front south-west view of the anti-snoring trampoline pillow with multiple options of headrest cushion.

Referring now to the FIG. 2 drawings, this front and south-west view of the preferred embodiment respectfully provides a more visible 3-dimensional view of the invention whereas the means of customized headrest cushions denoted as 50, 52 and 54 are displayed in three different designs that are inner changeable be the means of being attached to the base headrest referenced in FIG. 1 by numeral number 40, to provide the most effective setting to support the head and neck, aiming to reduce snoring.

The means of customized headrest cushions referenced by numeral number 50 in FIG. 2, discloses a headrest cushion having two equally leveled upper side opposite of each other formed with a center depression having a flat bottom wall with means of ability to be fasten to the base headrest of 40, and upwardly and outwardly curved side and end walls blending in streamlined fashion with the upper side and being formed a conventional flat. The headrest cushion referenced by numeral number 52, displays the same features as reference 50 with addition of the right-upper side being upwardly raised with respect to the left-upper side with the means of guiding the head position to the left side. The headrest cushion referenced by numeral number 54, displays the same features as reference 52 with addition of the left-upper side being upwardly raised with respect to the right-upper side with the means of guiding the head position to the right side.

Figure 3:
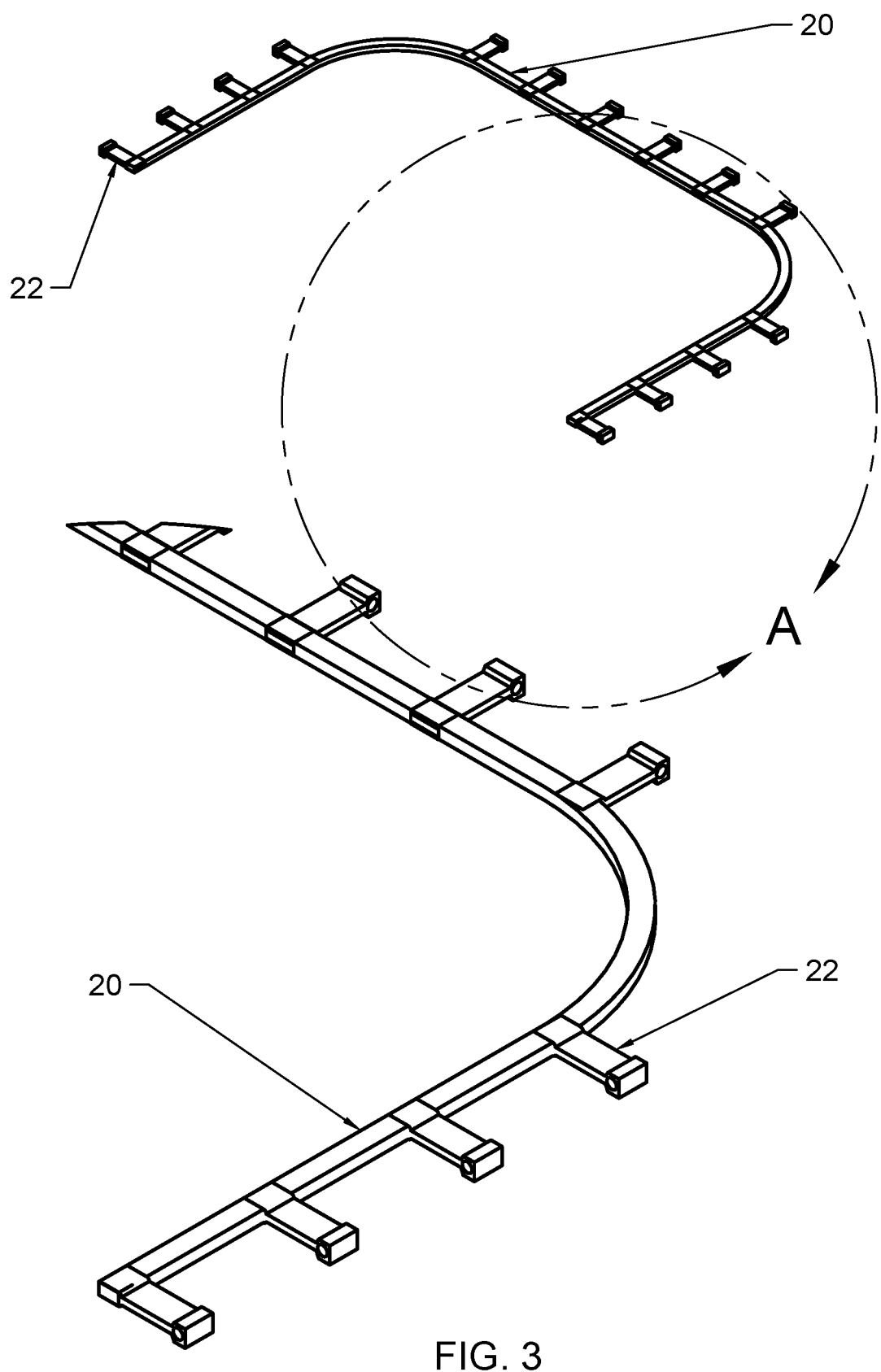
FIG. 3 illustrates a front south-west view of the elastic band with enlarged corner section.

Referring now to the drawings in FIG. 3, the preferred embodiment of the current invention comprises a elastic band referenced by numeral number 20 with the means of being connected by and through plurality of tension members referenced by numeral number 22 extended-out with an enlarged shaped end to the frame of referenced 10 in FIG. 1 from one side and to the zipper referenced 30 in FIG. 1 from the opposite side. The said enlarged end of tension members denoted by referenced numeral number 22 are used to allow slide-in installation or removal of the elastic band from the said frame of referenced 10.

The said elastic band of the above, provides the necessary means of continues tension throughout all connected components of the preferred embodiment to prevent any surface area from going flat. The overall elasticity performance of the band and its members can vary based on their thickness, number of tension members and the elastic material make-up composition characteristics in addition to any indirect measures such as ambient temperature. The variant combination of the said characteristics results in three major performance comfort level. The said comfort levels can further be classified as; soft, medium and firm comfort levels. The higher the tension resistance is against applied downward pressure, the more firm the embodiment would behave and vice versa in case of soft comfort level. Based on disclosed comfort levels description, the user can select an elastic band to best match their comfort preferences while providing neck and head support.

It is to be noted that the disclosed description and design of the elastic band is only one variant of many possibilities, therefore the current invention is not limited to the above design as long as the functionality is delivered by the embodiment.

Figure 4:
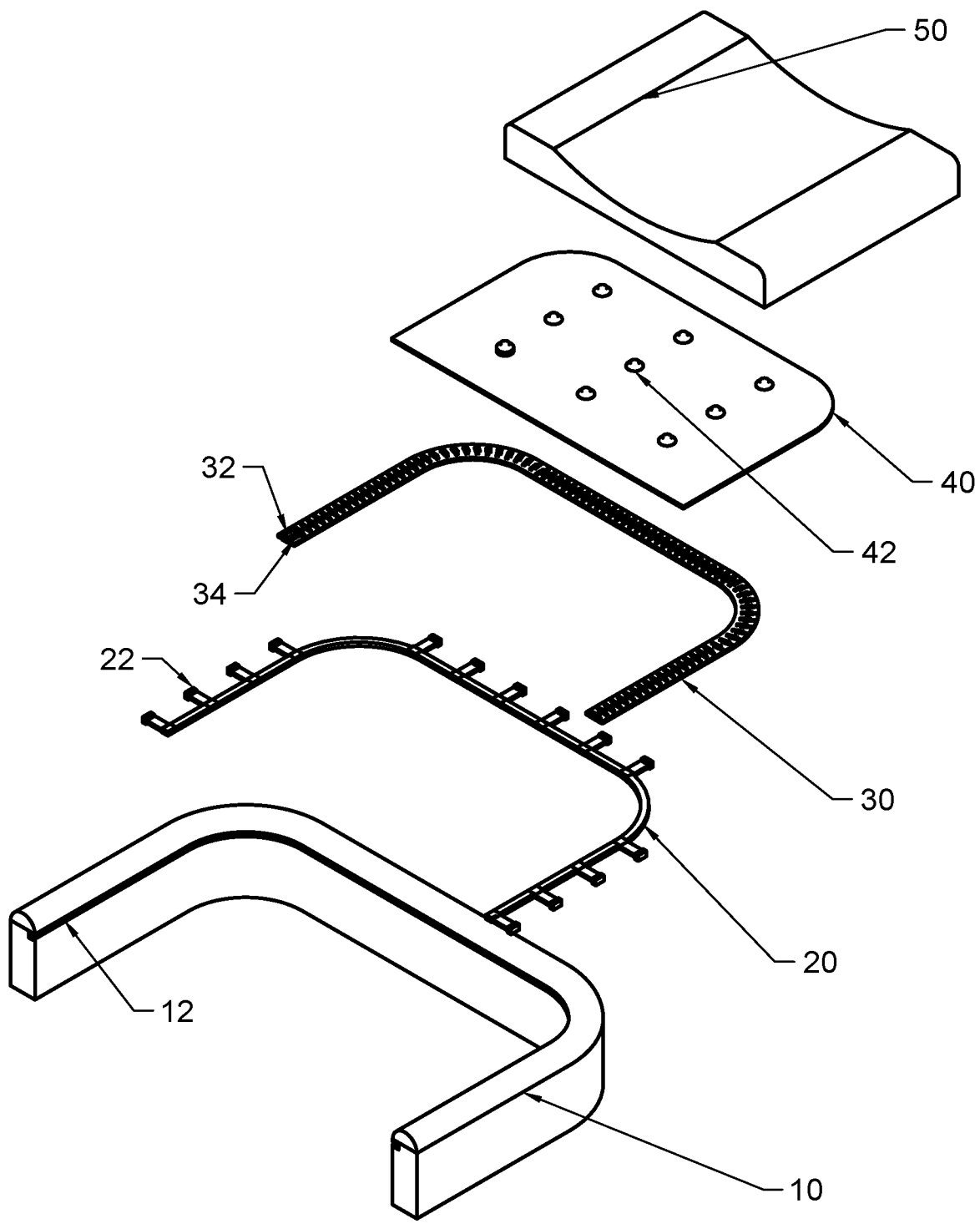
FIG. 4 illustrates an exploded view of components make-up of anti-snoring trampoline pillow.

Referring now to FIG. 4, is an exploded view of one preferred embodiment displaying components and their relative position in regards to one another. The said components are referenced by numeral number 10 known as the shaped rigid frame, referenced numeral number 20 known as elastic band, referenced numeral number 30, known as zipper, referenced numeral number 40, known as base headrest and referenced numeral number 50, known as customized headrest cushion.

In reference to FIG. 4, the preferred embodiment of the current invention comprises a zipper, referenced by numeral number 30 and its left zipper tape referenced as numeral number 32 with the means of being connected to the elastic band of referenced 20. The zipper tape of referenced 34 provides the means of being connected to the base headrest. The said zipper of referenced 30 provides the means of connectivity between the elastic band of reference 20 and the headrest of referenced 40. The said zipper allows the connected components to be disengaged, replaced or exchanged with other designated components.

In reference to FIG. 4, the preferred embodiment of the current invention comprises of a base headrest referenced by numeral number 40, provides the means of a designated surface area for the head and neck to rest on. The said base headrest with means of being connected from its outer edge to the zipper tape of referenced numeral 34 also includes the means for the customized headrest cushions of referenced 50 to be securely fastened to its surface as being demonstrated by referenced numeral number 42. Such means of attachment instrument includes but not limited to snap-buttons, Velcro tapes, pins, sliders, magnets, glue or any other commercially available methods of fasteners. The said base headrest surface in a preferred embodiment is perforated to allow air circulation and prevents the accumulation of excess heat that would otherwise cause discomfort. The referenced base headrest are formed of a material selected from the group consisting of man-made material, natural material, and any combinations thereof.

In reference to FIG. 4, the preferred embodiment of the current invention comprises of customized headrest cushions referenced by numeral number 50, provides the means of a designated surface area for the head and neck to rest on.

I claim:

1. A head support device and pillow comprising:
    a substantially u-shaped rigid frame comprising two substantially parallel arms each connected at one end to a rear member;
    an elastic band extending along an interior wall of said substantially u-shaped rigid frame and mounted to said interior wall by a plurality of tension members spaced apart along an inner edge of the elastic band;
    a base headrest support surface connected to said elastic band along a periphery of said base headrest support surface; and
    a headrest cushion secured to an upper side of said base headrest support surface whereby a user can rest their head and neck on the headrest.

2. The head support device and pillow of claim 1, wherein said u-shaped rigid frame comprises an extruded channel extending along the interior wall from a distal end of one of said two substantially parallel arms to a distal end of the other one of said two substantially parallel arms.

3. The head support device and pillow of claim 2, wherein said plurality of tension members each have an end mounted within the extruded channel.

4. The head support device and pillow of claim 1, wherein a fastener connects the periphery of the base headrest support surface to an outer edge of the elastic band.

5. The head support device and pillow of claim 4, wherein three edges of the periphery of the base head rest support surface are connected to the outer edge of the elastic band.

6. The head support device and pillow of claim 1, wherein at least on attachment secures the headrest cushion to the upper surface of the base headrest support surface.

7. The head support device and pillow of claim 1, wherein the headrest cushion comprises a substantially rectangular body portion having opposed parallel ends, an upper side and an underside, said upper side having left, right and central section's wherein the central section includes a concave depression and the underside has at least one connecting fastener for attaching said headrest cushion to the base headrest support surface.

8. The head support device and pillow of claim 7 wherein a thickness of at least one of said left and right sections is at least twice that of said central section so as to help locate and retain a user's head and neck within the concave depression.

\* \* \* \* \*